United States Patent
Kim et al.

(10) Patent No.: US 10,604,459 B2
(45) Date of Patent: Mar. 31, 2020

(54) CATALYTIC BODY COATED WITH METAL OXIDE, METHOD OF MANUFACTURING THE SAME, AND METHOD OF PREPARING 1,3-BUTADIENE USING THE SAME

(71) Applicant: Korea Kumho Petrochemical Co., Ltd., Seoul (KR)

(72) Inventors: Yun Jung Kim, Daejeon (KR); Jae Woo Kim, Daejeon (KR); Yong Hee Yun, Sejong-si (KR); Ji Won Park, Daejeon (KR); Kyoung Ho Row, Daejeon (KR)

(73) Assignee: KOREA KUMHO PETROCHEMICAL CO., LTD., Seoul (KR)

( * ) Notice: Subject to any disclaimer, the term of this patent is extended or adjusted under 35 U.S.C. 154(b) by 0 days.

(21) Appl. No.: 16/029,833

(22) Filed: Jul. 9, 2018

(65) Prior Publication Data
US 2019/0016649 A1    Jan. 17, 2019

(30) Foreign Application Priority Data
Jul. 13, 2017  (KR) .................. 10-2017-0088996

(51) Int. Cl.
*C07C 5/32*   (2006.01)
*C07C 11/167*  (2006.01)
(Continued)

(52) U.S. Cl.
CPC .............. *C07C 5/322* (2013.01); *B01J 6/008* (2013.01); *B01J 21/04* (2013.01); *B01J 21/063* (2013.01); *B01J 21/08* (2013.01); *B01J 23/28* (2013.01); *B01J 23/78* (2013.01); *B01J 35/08* (2013.01); *B01J 37/0207* (2013.01);
(Continued)

(58) Field of Classification Search
CPC ...... C07C 5/322; C07C 5/3332; C07C 11/167; B01J 6/008; B01J 21/04; B01J 21/063; B01J 21/08; B01J 23/28; B01J 23/78; B01J 35/08; B01J 37/0207; B01J 37/088
See application file for complete search history.

(56) References Cited

U.S. PATENT DOCUMENTS

| 3,145,183 A | * | 8/1964 | Fisher ................ B01J 21/16 502/439 |
| 2001/0031693 A1 | * | 10/2001 | Hoke ................ B01D 53/02 502/80 |

FOREIGN PATENT DOCUMENTS

| KR | 10-2012-0009687 A | 2/2012 |
| KR | 10-2015-0003214 A | 1/2015 |

OTHER PUBLICATIONS

Zhang et al(Effect of intermediate layer on the activity and adhesion stability of metal monolith supported LaMn-hexaaluminate catalyst for methane combustion, J. Rare. Earths, vol. 29, No. 8, (2011) pp. 758) (Year: 2011).*

* cited by examiner

*Primary Examiner* — Melvin C. Mayes
*Assistant Examiner* — Michael Forrest
(74) *Attorney, Agent, or Firm* — Novick, Kim & Lee, PLLC; Jae Youn Kim

(57) ABSTRACT

According to an embodiment of the present invention, there are provided a catalytic body, a method of manufacturing the same, and a method of preparing 1,3-butadiene using the same. The catalytic body includes an inactive support; an intermediate layer disposed on a surface of the inactive support; and an active layer disposed on a surface of the intermediate layer, wherein the active layer includes catalyst powder and a binder.

19 Claims, 1 Drawing Sheet

(51) Int. Cl.
*B01J 35/08* (2006.01)
*B01J 37/02* (2006.01)
*B01J 23/28* (2006.01)
*B01J 21/08* (2006.01)
*B01J 21/06* (2006.01)
*B01J 6/00* (2006.01)
*B01J 21/04* (2006.01)
*C07C 5/333* (2006.01)
*B01J 23/78* (2006.01)
*B01J 37/08* (2006.01)

(52) U.S. Cl.
CPC ............ *B01J 37/088* (2013.01); *C07C 5/3332* (2013.01); *C07C 11/167* (2013.01); *B01J 2523/22* (2013.01); *B01J 2523/27* (2013.01); *B01J 2523/54* (2013.01); *B01J 2523/842* (2013.01); *C07C 2523/78* (2013.01)

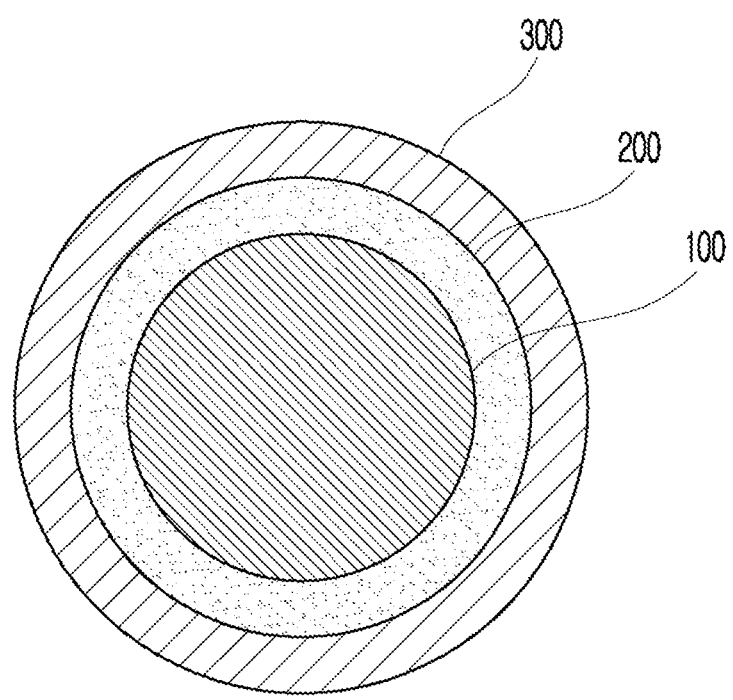

CATALYTIC BODY COATED WITH METAL OXIDE, METHOD OF MANUFACTURING THE SAME, AND METHOD OF PREPARING 1,3-BUTADIENE USING THE SAME

CROSS-REFERENCE TO RELATED APPLICATION

This application claims priority to and the benefit of Korean Patent Application No. 10-2017-0088996, filed on Jul. 13, 2017, the disclosure of which is incorporated herein by reference in its entirety.

BACKGROUND

1. Field of the Invention

The present invention relates to a catalytic body coated with a metal oxide, a method of manufacturing the same, and a method of preparing 1,3-butadiene using the same.

2. Discussion of Related Art

As catalysts used in oxidative dehydrogenation of n-butene, there are ferrite-based, bismuth molybdate-based, and tin-based catalysts. These catalysts are metal oxide catalysts and are generally synthesized in a powder form. When the flow rate of the powder-type catalyst is above a predetermined flow rate in a fixed-bed reactor, the pressure inside the reactor is drastically dropped, and thus it is difficult to apply the powder-type catalyst to the process. Therefore, the powder-type catalyst is not applicable without a compacting process. Also, since heat is not smoothly transferred, the temperature inside the catalyst significantly increases locally to induce catalyst sintering and make it difficult to control the reaction.

A catalytic body may take various forms such as extruded, pressed, and coated forms according to the manufacturing method and conditions. Among them, extruded and pressed catalytic bodies are most widely used, but as the particle size of the catalyst increases through compacting, surface area thereof significantly decreases and the chance for a catalyst particle in the body to participate in a reaction is reduced, and thus the catalytic bodies have degraded catalytic activity compared to the powder-type catalyst.

The coated catalytic body is more economical and advantageous in terms of catalyst efficiency compared to an extruded or pressed catalytic body because a usage amount of a catalyst can be significantly reduced, and an amount of the catalyst that does not participate in the reaction can also be reduced. In particular, when the oxidative dehydrogenation of n-butene, which is an exothermic reaction, is carried out using the coated catalytic body, a support in the catalytic body serves as a heat diluent material which dissipates the released heat. That is, a side reaction is suppressed by controlling the release of heat, and thus 1,3-butadiene may be prepared with a high yield.

In this regard, Korean Unexamined Patent Publication No. 2015-0003214 discloses a method in which a coated catalyst is used to suppress an increase in temperature of a catalyst bed and improve the yield of 1,3-butadiene more effectively compared to when an extruded catalyst is used. However, since the type of support for the catalytic body is limited to a support type in which the volume of the micropores accounts for 80% or more of the total pore volume, there is a problem in that a material which is not abundant in pores and has a low specific surface area, such as α-alumina and the like, cannot be used as a support.

In addition, Korean Unexamined Patent Publication No. 2012-0009687 discloses that the release of heat may be easily controlled by using a coated catalyst prepared using a support with high thermal conductivity and a binder in the oxidative dehydrogenation of n-butene. However, in this case, a large amount of a binder is used, causing the relative proportion of catalyst powder to decrease and the occurrence of side reactions due to the binder to increase, and thus the catalytic activity may be degraded.

SUMMARY OF THE INVENTION

The present invention is designed to solve the problems of the prior art, and it is an object of the present invention to provide a catalytic body which can be prepared using a more wide selection of support, exhibits excellent adhesion and binding between the catalyst powder and a support even when a small amount of a binder is used, and has excellent activity for oxidative dehydrogenation of n-butene; and a method of manufacturing the same.

According to one aspect of the present invention, there is provided a catalytic body which includes an inactive support; an intermediate layer disposed on a surface of the inactive support; and an active layer disposed on a surface of the intermediate layer, wherein the active layer includes catalyst powder and a binder.

According to an embodiment, the inactive support may have a porosity of 70 vol % or less.

According to an embodiment, the inactive support may be of one shape selected from the group consisting of a spherical shape, a cylindrical shape, a ring shape, a platy shape, and a combination of two or more thereof.

According to an embodiment, the inactive support may be one selected from the group consisting of alumina, silica, zirconia, silicon carbide, cordierite, and a combination of two or more thereof.

According to an embodiment, the intermediate layer may consist of one selected from the group consisting of alumina, silica, kaolin, $TiO_2$, ZnO, bentonite, and a combination of two or more thereof.

According to an embodiment, the intermediate layer may have a weight of 3 to 15 g/L with respect to a volume of the inactive support.

According to an embodiment, the catalyst powder may be an oxide derived from one selected from the group consisting of iron, magnesium, manganese, zinc, bismuth, molybdenum, and a combination of two or more thereof.

According to an embodiment, the binder may include an inorganic binder, and the inorganic binder may be included in an amount of 5 to 20 wt % with respect to the total weight of the catalyst powder and the inorganic binder.

According to an embodiment, the inorganic binder may be one selected from the group consisting of alumina, silica, sodium silicate, aluminum silicate, calcium silicate, calcium carbonate, barium carbonate ($BaCO_3$), kaolin, mica, $TiO_2$, ZnO, iron oxide, bentonite, and a mixture of two or more thereof.

According to an embodiment, the catalyst powder may have a weight of 200 to 500 g/L with respect to a volume of the inactive support.

According to another aspect of the present invention, there is provided a method of manufacturing the catalytic body, which includes (a) mixing an inactive support and a sol, followed by drying and thermal treatment to form an intermediate layer on a surface of the inactive support; (b)

dissolving two or more types of metal salts in a first solvent to prepare a first solution, and preparing catalyst powder by pyrolyzing the first solution while spraying the first solution into a reactor using a carrier gas or by adding a co-precipitant to the first solution and then performing drying and thermal treatment; (c) mixing the catalyst powder, a binder, and a second solvent to prepare a second solution; and (d) mixing the product of the step (a) and the second solution, followed by drying and thermal treatment to form an active layer including the catalyst powder on a surface of the intermediate layer.

According to an embodiment, the inactive support may have a porosity of 70 vol % or less.

According to an embodiment, the inactive support may be of one shape selected from the group consisting of a spherical shape, a cylindrical shape, a ring shape, a platy shape, and a combination of two or more thereof.

According to an embodiment, the inactive support may be one selected from the group consisting of alumina, silica, zirconia, silicon carbide, cordierite, and a combination of two or more thereof.

According to an embodiment, the intermediate layer may consist of one selected from the group consisting of alumina, silica, kaolin, $TiO_2$, ZnO, bentonite, and a combination of two or more thereof.

According to an embodiment, the intermediate layer may have a weight of 3 to 15 g/L with respect to a volume of the inactive support.

According to an embodiment, the metal salt may be a nitrate derived from one selected from the group consisting of iron, magnesium, manganese, zinc, bismuth, molybdenum, and a combination of two or more thereof.

According to an embodiment, the co-precipitant may be sodium hydroxide, ammonia, or a combination thereof.

According to an embodiment, the pyrolysis may be carried out at 500 to 900° C.

According to an embodiment, the binder may include an inorganic binder, and the inorganic binder may be included in an amount of 5 to 20 wt % with respect to the total weight of the catalyst powder and the inorganic binder.

According to an embodiment, the inorganic binder may be one selected from the group consisting of alumina, silica, sodium silicate, aluminum silicate, calcium silicate, calcium carbonate, barium carbonate ($BaCO_3$), kaolin, mica, $TiO_2$, ZnO, iron oxide, bentonite, and a mixture of two or more thereof.

According to an embodiment, the catalyst powder may have a weight of 200 to 500 g/L with respect to a volume of the inactive support.

According to still another aspect of the present invention, there is provided a method of preparing 1,3-butadiene by the oxidative dehydrogenation of n-butene in the presence of the catalytic body.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIG. 1 is a schematic diagram of the structure of a catalytic body according to an embodiment of the present invention.

DETAILED DESCRIPTION OF EXEMPLARY EMBODIMENTS

Hereinafter, exemplary embodiments of the present invention will be described in detail with reference to the accompanying drawings. However, it should be understood that the present invention can be implemented in various forms, and that it is not intended to limit the present invention to the exemplary embodiments. Also, in the drawings, descriptions of parts unrelated to the detailed description are omitted to clearly describe the present invention. Throughout the specification, like numbers refer to like elements.

Throughout the specification, a certain part being "connected" to one other part means that the certain part is "directly connected" to the other part or that the certain part is "indirectly connected" to the other part through another member interposed between the two parts. Also, a certain part "including" a certain element signifies that the certain part may further include, instead of excluding, another element unless particularly indicated otherwise.

Catalytic Body

FIG. 1 is a schematic diagram of the structure of a catalytic body according to an embodiment of the present invention. Referring to FIG. 1, a catalytic body according to one aspect of the present invention includes an inactive support 100; an intermediate layer 200 disposed on a surface of the inactive support 100; an active layer 300 disposed on a surface of the intermediate layer 200, wherein the active layer 300 includes catalyst powder and a binder.

The inactive support 100 may include a plurality of pores formed on the inside and surfaces thereof. In this case, the inactive support 100 may have a porosity of 70 vol % or less, preferably 50 vol % or less, and more preferably 30 wt % or less. When the inactive support 100 has a porosity of greater than 70 vol %, the catalyst powder supported in any region inside the support may not participate in the reaction, and since it is difficult to dissipate released heat before another reaction takes place, an unwanted side reaction may occur.

The inactive support 100 may be of one shape selected from the group consisting of a spherical shape, a cylindrical shape, a ring shape, a platy shape, and a combination of two or more thereof, and is preferably a spherical shape, but the present invention is not limited thereto. In this case, pores of the inactive support 100 may be distributed in the vicinity of the surface of the inactive support 100, for example, throughout a region from the surface of the inactive support 100 to a specific depth below the surface, and may not exist in the vicinity of the center. That is, pores of the inactive support 100 may be present only in the vicinity of the surface thereof, and, in this case, the inactive support 100 may be a "solid-type" inactive support which does not substantially include a pore therein. The solid-type inactive support 100 may be one selected from the group consisting of alumina, silica, zirconia, silicon carbide, cordierite, and a combination of two or more thereof, and is preferably alumina and more preferably α-alumina, but the present invention is not limited thereto.

The catalytic body may include the intermediate layer 200 disposed on the surface of the inactive support 100 to reinforce adhesion and binding between the inactive support 100 and the active layer 300.

The intermediate layer 200 may consist of one selected from the group consisting of alumina, silica, kaolin, $TiO_2$, ZnO, bentonite, and a combination of two or more thereof, preferably alumina, and more preferably γ-alumina, but the present invention is not limited thereto. For example, the intermediate layer 200 consisting of γ-alumina may be formed by thermally treating an alumina sol applied on the inactive support 100.

The alumina sol may be prepared through a series of processes which include hydrolyzing one or more type of aluminum precursors selected from boehmite, aluminum salts, and aluminum alkoxides in the present of water and condensing the products to form boehmite particles and adding an acid to the boehmite particles to peptize the boehmite particles.

The aluminum salt may be one selected from the group consisting of aluminum nitrate, aluminum chloride, aluminum sulfate, aluminum phosphide, and a mixture of two or more thereof, but the present invention is not limited thereto.

The aluminum alkoxide may be one selected from the group consisting of aluminum ethoxide, aluminum isopropoxide, aluminum sec-butoxide, and a mixture of two or more thereof, but the present invention is not limited thereto.

The water may be used in an amount of 1 to 20 moles per 1 mole of the aluminum precursor. When the water is used in an amount of less than 1 mole, it is difficult to form the alumina sol due to an insufficient amount of a solvent, and the resulting material may not be uniformly combined with the inactive support due to high viscosity. On the other hand, when the water is used in an amount of greater than 20 moles, it is difficult to uniformly apply the alumina sol on the surface of the inactive support due to a relatively long distance between particles of the alumina sol and the inactive support.

The acid may be one selected from the group consisting of nitric acid ($HNO_3$), hydrochloric acid (HCl), sulfuric acid ($H_2SO_4$), acetic acid ($CH_3COOH$), phosphoric acid ($H_3PO_4$), and a mixture of two or more thereof, and is preferably nitric acid, but the present invention is not limited thereto.

The acid may be used in an amount of 0.01 to 0.2 mole, preferably 0.05 to 0.15 mole, per 1 mole of the aluminum precursor, but the present invention is not limited thereto. The acid is added to peptize the boehmite particles.

When the acid is used in an amount of less than 0.01 mole per 1 mole of the aluminum precursor, particles of the alumina sol may not be well dispersed, and thus the alumina sol may not be uniformly combined with the inactive support. On the other hand, when the acid is used in an amount of greater than 0.2 mole, an excessive amount of electrolyte ions such as those of nitric acid or the like is adsorbed onto a particle surface, and thus it is difficult to uniformly apply the alumina sol on the surface of the inactive support 100.

The alumina sol applied on the surface of the inactive support 100 may be thermally treated to convert the alumina sol into γ-alumina, and the active layer 300 including the aforementioned catalyst powder may be strongly bound, adhered, and thus fixed to the surface of the intermediate layer 200 consisting of γ-alumina.

The thermal treatment may be carried out at 500 to 1,000° C., preferably 800° C., but the present invention is not limited thereto. When the thermal treatment is carried out at less than 500° C., the solvent in the alumina sol may not be sufficiently removed but remain as an impurity, and when the thermal treatment is carried out at greater than 1,000° C., a portion of the support may be deformed, and thus the support may become nonuniform.

In addition, the phase transition of alumina to γ-, δ-, θ-, or α-alumina occurs as ambient temperature increases, and this may result in a change in the specific surface area of particles. Specifically, since the specific surface area is significantly decreased as phase transition from γ-phase to α-phase occurs, the specific surface area of organic particles is significantly decreased upon pyrolysis under a condition of greater than 1,000° C., causing the binding between the intermediate layer and the active layer to be weakened.

The alumina sol may have a weight of 3 to 15 g/L, preferably 5 to 10 g/L, with respect to the volume of the inactive support. When the weight of the alumina sol is less than 3 g/L with respect to the volume of the inactive support, it is difficult for catalyst powder to be strongly bound and adhered due to an insufficient surface roughness of γ-alumina. On the other hand, when the weight of the alumina sol is greater than 15 g/L, a thickness of the intermediate layer increases so that an excessive amount of dust may be generated when the alumina sol is thermally treated, and the dust is applied together with the catalyst powder during a subsequent catalyst powder coating process so that an unwanted side reaction may occur.

The active layer 300 may be formed by applying a composition including catalyst powder, a binder, and a solvent onto a surface of the intermediate layer 200 consisting of γ-alumina, followed by drying and thermal treatment. Since the solvent included in the composition is removed during the drying and thermal treatment, the active layer 300 may substantially include the catalyst powder and the binder, and particularly, the catalyst powder may be uniformly distributed in the active layer 300.

The catalyst powder may be an oxide including one selected from the group consisting of iron, magnesium, manganese, zinc, bismuth, molybdenum, and a combination of two or more thereof at a predetermined ratio.

The binder may include an inorganic binder, and the inorganic binder may be included in an amount of 5 to 20 wt %, preferably 5 to 10 wt %, with respect to the total weight of the catalyst powder and the inorganic binder. When the inorganic binder is included in an amount of less than 5 wt %, the catalyst powder may be weakly bound to a support, and when the inorganic binder is included in an amount of greater than 20 wt %, the relative proportion of the catalyst powder decreases, and thus a catalytic body with low catalytic activity may be obtained.

The inorganic binder may be one selected from the group consisting of alumina, silica, sodium silicate, aluminum silicate, calcium silicate, calcium carbonate, barium carbonate ($BaCO_3$), kaolin, mica, $TiO_2$, ZnO, iron oxide, bentonite, and a mixture of two or more thereof, and is preferably kaolin, but the present invention is not limited thereto.

The binder may further include an organic binder. For example, the organic binder may be ethyl cellulose, methyl cellulose, or a derivative thereof, and is preferably methyl cellulose, but the present invention is not limited thereto. The organic binder serves to improve coating-forming ability and shaping ability of the active layer and reduce the risk of crack generation during drying.

In the catalytic body, the catalyst powder may have a weight of 200 to 500 g/L with respect to the volume of the inactive support. When the weight of the catalyst powder is less than 200 g/L, some catalyst powder particles applied on the support may be detached, disturbing the uniform distribution of catalyst powder. On the other hand, when the weight thereof is greater than 500 g/L, an active layer with an excessively large thickness is prepared such that catalyst powder particles disposed close to the intermediate layer cannot participate in the reaction, and since it is difficult to dissipate released heat before another reaction takes place, an unwanted side reaction may occur.

The thermal treatment of the active layer may be carried out at 500 to 650° C. When the thermal treatment is carried out at less than 500° C., the required strength may not be imparted to the active layer, and when the thermal treatment is carried out at greater than 650° C., a portion of the catalyst may undergo a phase change, and thus a desired level of catalytic activity may not be obtained.

Method of Manufacturing Catalytic Body

A method of manufacturing a catalytic body according to another aspect of the present invention may include (a) mixing an inactive support and a sol, followed by drying and thermal treatment to form an intermediate layer on a surface of the inactive support; (b) dissolving two or more types of metal salts in a first solvent to prepare a first solution, and preparing catalyst powder by pyrolyzing the first solution while spraying the first solution into a reactor using a carrier gas or by adding a co-precipitant to the first solution and then performing drying and thermal treatment; (c) mixing the catalyst powder, a binder, and a second solvent to prepare a second solution; and (d) mixing the product of the step (a) and the second solution, followed by drying and thermal treatment to form a coating including the catalyst powder on a surface of the intermediate layer.

In the step (a), the descriptions of the porosity, shape, and type of the inactive support, the type and preparation method of the sol, and a usage amount of the sol and a temperature of the thermal treatment required to form the intermediate layer are as described above.

In the step (b), two or more types of metal salts may be dissolved in a first solvent to prepare a first solution, and the first solution may be pyrolyzed while being sprayed into a reactor using a carrier gas to prepare catalyst powder. The metal salt may be a nitrate derived from one selected from the group consisting of iron, magnesium, manganese, zinc, bismuth, molybdenum, and a combination of two or more thereof, and is preferably iron nitrate or magnesium nitrate, but the present invention is not limited thereto.

For example, magnesium nitrate and iron nitrate may be dissolved in a first solvent to prepare a first solution, that is, a precursor solution. When the first solution is prepared, the temperature of the solution may be maintained at 10 to 80° C., preferably 15 to 60° C., and more preferably 25 to 40° C., to increase the solubility of each precursor. In this case, magnesium nitrate and iron nitrate may be mixed in such a way that the molar ratio of magnesium and iron is 1:1.5 to 2.5.

The nitrates derived from magnesium and iron may be magnesium nitrate and iron nitrate, respectively, but the present invention is not limited thereto, and one or more selected from the group consisting of sulfates, chlorides, and carbonates may also be used instead of each nitrate.

The first solvent may be a polar solvent and is preferably water, but the present invention is not limited thereto. When the first solvent is water, an impurity in the first solution is minimized, and thus the purity of a metal oxide catalyst, which is a final product, may be improved.

The carrier gas may be air. The air pressure may be 2 to 4 atm, preferably 3 atm. When the air pressure is less than 2 atm, the activity of the prepared catalyst does not meet the basic requirements for 1,3-butadiene preparation, and when the air pressure is greater than 4 atm, excessive costs are incurred, causing economic damage, and the catalytic activity may be degraded due to the formation of a solid solution or the deformation of a crystal structure.

The pyrolysis may be carried out at 500 to 900° C., preferably 700 to 800° C., and more preferably 750° C. When the pyrolysis is carried out at less than 500° C., a catalyst crystal suitable for the basic requirements required to prepare 1,3-butadiene may not be obtained, and when the pyrolysis is carried out at greater than 900° C., the catalyst may be melted to form a solid solution, or the crystal structure of the catalyst may be deformed.

As necessary, the catalyst powder prepared through the pyrolysis may be thermally treated at a predetermined temperature to remove remaining water, nitrate, and the like which are included in the catalyst powder, and accordingly, the purity of the catalyst powder may be further improved. Therefore, the selectivity for 1,3-butadiene and the purity of the catalyst may be improved.

The thermal treatment of catalyst powder may be carried out at 500 to 600° C., preferably 530 to 570° C., and more preferably 550° C. When the thermal treatment is carried out at less than 500° C., it is difficult to expect an improvement in the purity of the catalyst and the selectivity for 1,3-butadiene, and when the thermal treatment is carried out at greater than 600° C., the yield of 1,3-butadiene may be significantly decreased despite an improvement in the selectivity for 1,3-butadiene.

In addition, the thermal treatment of catalyst powder may be carried out for 1 to 10 hours, preferably, 2 to 6 hours. when the thermal treatment is carried out for less than 1 hour, it is difficult to expect an improvement in the purity of the catalyst and the selectivity for 1,3-butadiene, and when the thermal treatment is carried out for greater than 10 hours, the rate of conversion into 1,3-butadiene may be significantly decreased despite an improvement in the selectivity for 1,3-butadiene.

Meanwhile, in the step (b), two or more types of metal salts may be dissolved in a first solvent to prepare a first solution, and a co-precipitant may be added to the first solution, followed by drying and thermal treatment to prepare catalyst powder.

For example, magnesium nitrate and iron nitrate may be dissolved in a first solvent to prepare a first solution, that is, a precursor solution. When the first solution is prepared, the temperature of the solution may be maintained at 10 to 80° C., preferably 15 to 60° C., and more preferably 25 to 40° C., to increase the solubility of each precursor. In this case, magnesium nitrate and iron nitrate may be mixed in such a way that the molar ratio of magnesium and iron is 1:1.5 to 2.5.

In order to co-precipitate the metal ions dissolved in the first solution to form solid phases, a basic solution at a concentration of 1.0 to 10.0 M, for example, an aqueous sodium hydroxide solution and/or an aqueous ammonia solution at a concentration of 4 M may be added as a co-precipitant. When the concentration of the basic solution is less than 1.0 M, it is difficult to form the crystal structure of the catalyst powder, and when the concentration thereof is greater than 10.0 M, it is difficult to remove a metal ion bonded with a hydroxyl group (e.g., a Na ion in the case of sodium hydroxide) during washing, and thus the catalytic activity is degraded.

The basic solution is added at a rate adjusted such that the first solution maintains a constant pH of 6 to 10, and the resulting solution is stirred for 1 to 24 hours, preferably 6 to 20 hours, so that co-precipitation is sufficiently carried out.

The first solution thus stirred is subjected to phase separation for an enough time to obtain a solid-phase precipitate, and a solid sample is obtained from the precipitate using a vacuum filter or the like. The solid sample thus obtained may be dried at 70 to 200° C., preferably 100 to 180° C., for 12 to 48 hours, and the catalyst thus dried may be put in an electric furnace and thermally treated at 350 to 800° C., preferably 500 to 700° C., to obtain catalyst powder.

In the step (c), the catalyst powder, a binder, and a second solvent may be mixed to prepare a second solution. The second solvent may be a polar solvent and is preferably water, but the present invention is not limited thereto. When the second solvent is water, an impurity in the second solution is minimized, and thus the purity of a metal oxide catalyst, which is a final product, may be improved. The descriptions of a type and a content of the binder are as described above.

In the step (d), the product of the step (a) and the second solution may be mixed, dried, and thermally treated to form an active layer including catalyst powder on a surface of the intermediate layer. The descriptions of a usage amount of catalyst powder and a temperature of the thermal treatment which are required to form the active layer are as described above.

Hereinafter, embodiments of the present invention will be described in detail.

Example 1

20.5 kg of iron nitrate ($Fe(NO_3)_3 \cdot 9H_2O$, Samchun Chemical Co., Ltd, 98.5%) and 6.5 kg of magnesium nitrate ($Mg(NO_3)_2 \cdot 6H_2O$, Samchun Chemical Co., Ltd, 98%) were added to distilled water, and the mixture was stirred at room temperature for 2 hours so as to be sufficiently dissolved to prepare a solution containing magnesium and iron mixed at a molar ratio of 1:2. The solution thus prepared was pyrolyzed while being sprayed at a rate of 3.0 L per hour into a reactor of a spray pyrolysis device using air as a carrier gas. In this case, the spray pyrolysis was carried out under conditions of an air pressure of 3 atm and a temperature inside the reactor of 750° C. to prepare magnesium-iron ferrite metal oxide catalyst powder.

1.76 g of boehmite, 4.5 g of water, and 0.225 g of nitric acid were mixed to prepare an alumina sol. 300 mL of an α-alumina ball was added thereto and rotated such that the alumina sol was uniformly adhered to the ball. Subsequently, the resulting ball was dried at room temperature and 80° C. for 8 hours, and then thermally treated at 800° C. for 4 hours to prepare a ball-shaped α-alumina support coated with γ-alumina (Weight of alumina sol applied/Volume of α-alumina ball=5 g/L).

Next, 95.3 g of the magnesium-iron ferrite metal oxide catalyst powder, 10.5 g of kaolin, 2.1 g of methyl cellulose, and 16.2 g of water were homogeneously mixed, and 300 mL of the ball-shaped α-alumina support coated with γ-alumina was added thereto and then rotated to apply the catalyst powder onto γ-alumina. Subsequently, the resulting support was dried at room temperature and 80° C. for 8 hours, and then thermally treated at 550° C. for 4 hours to manufacture a ball-shaped catalytic body coated with a ferrite-based metal oxide (Weight of catalyst powder applied/Volume of α-alumina ball coated with alumina sol=300 g/L).

Example 2

A catalytic body was manufactured in the same manner as in Example 1 except that the weight of alumina sol applied/the volume of α-alumina ball was changed to 3 g/L.

Example 3

A catalytic body was manufactured in the same manner as in Example 1 except that the weight of alumina sol applied/the volume of α-alumina ball was changed to 10 g/L.

Example 4

A catalytic body was manufactured in the same manner as in Example 1 except that the weight of alumina sol applied/the volume of α-alumina ball was changed to 15 g/L.

Example 5

A catalytic body was manufactured in the same manner as in Example 1 except that the weight of catalyst powder applied/the volume of α-alumina ball coated with an alumina sol was changed to 200 g/L.

Example 6

A catalytic body was manufactured in the same manner as in Example 1 except that the weight of catalyst powder applied/the volume of α-alumina ball coated with an alumina sol was changed to 500 g/L.

Example 7

A catalytic body was manufactured in the same manner as in Example 1 except that the amount of kaolin with respect to the total weight of magnesium-iron ferrite metal oxide catalyst powder and kaolin was changed to 5 wt %.

Example 8

A catalytic body was manufactured in the same manner as in Example 1 except that the amount of kaolin with respect to the total weight of magnesium-iron ferrite metal oxide catalyst powder and kaolin was changed to 20 wt %.

Example 9

A catalytic body was manufactured in the same manner as in Example 1 except that magnesium-iron ferrite metal oxide catalyst powder was prepared by the following method.

2.1 kg of iron nitrate ($Fe(NO_3)_3 \cdot 9H_2O$, Samchun Chemical Co., Ltd, 98.5%) and 0.7 kg of magnesium nitrate ($Mg(NO_3)_2 \cdot 6H_2O$, Samchun Chemical Co., Ltd, 98%) were added to distilled water, and the mixture was stirred at room temperature for 2 hours so as to be sufficiently dissolved to prepare a solution containing magnesium and iron mixed at a molar ratio of 1:2. An aqueous 4 M sodium hydroxide solution was added to the solution at room temperature while stirring until a pH of 9.0 was reached to prepare a co-precipitation solution of $Mg(OH)_2$ and $Fe(OH)_3$. The co-precipitation solution was subjected to a hydrothermal reaction at room temperature for 3 hours, at 60° C. for 6 hours, and at 90° C. for 12 hours. A co-precipitated metal oxide was filtered using a Buchner funnel and a vacuum filter, sufficiently washed with distilled water, dried at 120° C. for 24 hours, and thermally treated in a burning furnace at 650° C. for 4 hours to prepare magnesium-iron ferrite metal oxide catalyst powder.

Comparative Example 1

1,118 g of the magnesium-iron ferrite metal oxide catalyst prepared in Example 1, 35 g of methyl cellulose, 59 g of kaolin, and 300 g of water were homogeneously mixed at room temperature and then extruded using a twin-screw extruder to form a cylindrical pellet having a diameter of 3 mm and a length of 3 to 5 mm. The magnesium-iron ferrite metal oxide catalyst thus extruded was dried at room temperature and 110° C. for 24 hours, and then thermally treated at 550° C. for 4 hours to manufacture a catalytic body.

Comparative Example 2

A catalytic body was manufactured in the same manner as in Example 1 except that the process of coating an α-alumina ball with an alumina sol was omitted.

Comparative Example 3

A catalytic body was manufactured in the same manner as in Example 1 except that the weight of alumina sol applied/the volume of α-alumina ball was changed to 1 g/L.

Comparative Example 4

A catalytic body was manufactured in the same manner as in Example 1 except that the weight of alumina sol applied/the volume of α-alumina ball was changed to 20 g/L.

Comparative Example 5

A catalytic body was manufactured in the same manner as in Example 1 except that the weight of catalyst powder applied/the volume of α-alumina ball coated with an alumina sol was changed to 50 g/L.

Comparative Example 6

A catalytic body was manufactured in the same manner as in Example 1 except that the weight of catalyst powder applied/the volume of α-alumina ball coated with an alumina sol was changed to 100 g/L.

Comparative Example 7

A catalytic body was manufactured in the same manner as in Example 1 except that the weight of catalyst powder applied/the volume of α-alumina ball coated with an alumina sol was changed to 800 g/L.

Comparative Example 8

A catalytic body was manufactured in the same manner as in Example 1 except that the amount of kaolin with respect to the total weight of magnesium-iron ferrite metal oxide catalyst powder and kaolin was changed to 3 wt %.

Comparative Example 9

A catalytic body was manufactured in the same manner as in Example 1 except that the amount of kaolin with respect to the total weight of magnesium-iron ferrite metal oxide catalyst powder and kaolin was changed to 50 wt %.

Experimental Example

Each of the catalytic bodies prepared in Examples and Comparative Examples was filled in a stainless reactor having a diameter of 23 mm so as to have a space velocity of 400 h$^{-1}$, and activated at 370° C. while allowing air to flow therethrough. A gas containing n-butene, oxygen, and steam mixed at a mixing ratio of 8.6 vol %:26.7 vol %:64.7 vol % and a mass flow controller were used to perform oxidative dehydrogenation at 370° C. to prepare 1,3-butadiene. The reaction apparatus was designed such that steam among the reactants was initially supplied as water using a micro-metering pump but vaporized into steam for a set preheating period before being injected together with other reactants into the fixed-bed reactor.

The catalytic activity was analyzed by transferring the product produced by the oxidative dehydrogenation to a gas chromatography equipped with a thermal conductivity detector and a flame ionic detector from 30 minutes after the reactant was passed through a catalyst bed. The C4 mixture used as the reactant was 100% 1-butene.

A conversion rate of n-butene, a yield of 1,3-butadiene, and a yield of $CO_2$ as measured after 20 hours of the oxidative dehydrogenation are shown in the following Table 1. A conversion rate of n-butene, a yield of 1,3-butadiene, and a yield of $CO_2$ were calculated by the following Equations 1 to 3, respectively.

$n$-Butene conversion rate [Equation 1]

$$n\text{-Butene conversion rate (\%)} = \frac{\text{Weight of } n\text{-butene reacted}}{\text{Weight of } n\text{-butene injected}} \times 100$$

1,3-Butadiene yield [Equation 2]

$$1,3\text{-Butadiene yield (\%)} = \frac{\text{Weight of 1,3-butadiene produced}}{\text{Weight of } n\text{-butene injected}} \times 100$$

$CO_2$ yield [Equation 3]

$$CO_2 \text{ yield (\%)} = \frac{\text{Weight of } CO_2 \text{ produced}}{\text{Weight of } n\text{-butene injected}} \times 100$$

TABLE 1

| Samples | Amount of alumina sol applied (g/L) | Amount of catalyst powder applied (g/L) | Amount of inorganic binder (wt %) | n-Butene conversion rate (%) | 1,3-Butadiene yield (%) | $CO_2$ yield (%) |
|---|---|---|---|---|---|---|
| Example 1 | 5 | 300 | 10 | 66.8 | 58.1 | 5 |
| Example 2 | 3 | 300 | 10 | 66.2 | 57.3 | 5.1 |
| Example 3 | 10 | 300 | 10 | 66.4 | 57.5 | 5 |
| Example 4 | 15 | 300 | 10 | 66.0 | 57.1 | 5.1 |
| Example 5 | 5 | 200 | 10 | 66.5 | 57.6 | 5 |
| Example 6 | 5 | 500 | 10 | 66.8 | 57.0 | 5.3 |
| Example 7 | 5 | 300 | 5 | 66.5 | 57.9 | 5 |
| Example 8 | 5 | 300 | 20 | 66.2 | 57.5 | 5.1 |
| Example 9 | 5 | 300 | 10 | 64.3 | 55.0 | 5.0 |
| Comparative Example 1 | 0 | 1100 | 10 | 65.8 | 50.6 | 6.5 |
| Comparative Example 2 | 0 | 300 | 10 | 52.1 | 42.1 | 3.4 |
| Comparative Example 3 | 1 | 300 | 10 | 55.2 | 48.0 | 3.9 |
| Comparative Example 4 | 20 | 300 | 10 | 63.0 | 51.0 | 5.5 |

TABLE 1-continued

| Samples | Amount of alumina sol applied (g/L) | Amount of catalyst powder applied (g/L) | Amount of inorganic binder (wt %) | n-Butene conversion rate (%) | 1,3-Butadiene yield (%) | $CO_2$ yield (%) |
|---|---|---|---|---|---|---|
| Comparative Example 5 | 5 | 50 | 10 | 36.3 | 33.8 | 1.8 |
| Comparative Example 6 | 5 | 100 | 10 | 40.2 | 35.1 | 2.3 |
| Comparative Example 7 | 5 | 800 | 10 | 64.0 | 53.0 | 5.6 |
| Comparative Example 8 | 5 | 300 | 3 | 46.1 | 40.2 | 3.1 |
| Comparative Example 9 | 5 | 300 | 50 | 53.8 | 44.4 | 5.9 |

Referring to Table 1, the catalytic bodies (Examples 1 to 9) manufactured by applying a predetermined amount of an alumina sol onto a surface of a ball-shaped solid α-alumina support and then applying a predetermined amount of catalyst powder resulted in a higher yield of 1,3-butadiene and a lower yield of $CO_2$ compared to the extruded catalytic body (Comparative Example 1). The catalytic body (Comparative Example 2) in which an alumina sol was not applied and the catalytic body (Comparative Example 3) in which the amount of alumina sol applied was below the predetermined range exhibited a low conversion rate of n-butene because catalyst powder was detached from the support due to the low adhesion of the catalyst powder, and the catalytic body in which the amount of alumina sol applied exceeded the predetermined range (Comparative Example 4) did not exhibit an improved catalytic activity.

In addition, the catalytic bodies in which the amount of catalyst powder applied was below the predetermined range (Comparative Examples 5 and 6) exhibited a low conversion rate of n-butene because it was difficult to uniformly apply catalyst powder onto the surface of the support, and the catalyst powder was detached from the support, and the catalytic body in which the amount of catalyst powder applied exceeded the predetermined range (Comparative Example 7) resulted in a high yield of $CO_2$ due to a consecutive reaction as caused by the formation of an active layer with a large thickness as in Comparative Example 1.

Additionally, the catalytic body in which the amount of the inorganic binder was below a predetermined range (Comparative Example 8) exhibited a low conversion rate of n-butene because the catalyst powder was detached from the support due to the low adhesion of the active layer, and the catalytic body in which the amount of the inorganic binder exceeded the predetermined range (Comparative Example 9) resulted in a high yield of $CO_2$ due to a side reaction caused by the inorganic binder.

From these results, it can be seen that since catalyst powder is present only on the surface of the support, when the catalytic bodies according to Examples 1 to 9 participate in the oxidative dehydrogenation of n-butene, consecutive reactions occurring in the catalytic body can be suppressed to increase the utilization efficiency of oxygen compared to when a conventional extruded catalyst body (Comparative Example 1) is used, and side reactions can be suppressed to reduce the amount of heat released, and accordingly, the conversion rate of n-butene and the yield of 1,3-butadiene can be improved. In particular, by adjusting the amounts of alumina sol applied onto the support, catalyst powder, and inorganic binder to be mixed with catalyst powder within their respective predetermined ranges, the aforementioned effects can be further enhanced.

A catalytic body according to one aspect of the present invention includes an intermediate layer interposed between an inactive support and an active layer, and thus adhesion and binding between the active layer and the inactive support are so strong that the catalytic activity can be maintained for a long period.

In addition, since the catalyst powder included in the active layer is present only on the surface of the inactive support, when the catalytic body participates in the oxidative dehydrogenation of n-butene, consecutive reactions occurring in the catalytic body can be suppressed to increase utilization efficiency of oxygen compared to when a conventional extruded or pressed catalyst is used, and side reactions can be suppressed to reduce the amount of heat released, and the conversion rate of n-butene and the yield of 1,3-butadiene can be improved.

Additionally, the active layer is substantially adhered to the surface of the intermediate layer previously formed on the surface of the inactive support, so that a type of applicable inactive support can be diversified without limitations set by the porosity and specific surface area of the inactive support.

In addition, a method of manufacturing a catalytic body according to another aspect of the present invention can significantly reduce the amount of a binder used to manufacture a catalytic body compared to a conventional method, and thus it is economically advantageous.

The above description of the present invention is only exemplary, and it will be understood by those skilled in the art that various modifications can be made without departing from the scope of the present invention and changing essential features. Therefore, the above-described embodiments should be considered as only illustrative in all aspects and not for purposes of limitation. For example, each component described as a single body may be realized in a distributed manner, and similarly, components that are described as being distributed may be realized in a combined manner.

The scope of the present invention is defined by the appended claims and encompasses all modifications and alterations derived from meanings, the scope and equivalents of the appended claims.

LIST OF REFERENCE NUMERALS

100: inactive support
200: intermediate layer
300: active layer

What is claimed is:

1. A catalytic body comprising:
an inactive support;
an intermediate layer disposed on a surface of the inactive support; and
an active layer disposed on a surface of the intermediate layer,
wherein:
the active layer includes catalyst powder and a binder;
the binder includes an inorganic binder;
the inorganic binder is included in an amount of 5 to 20 wt % with respect to a total weight of the catalyst powder and the inorganic binder; and
the catalyst powder has a weight of 200 to 500 g/L with respect to a volume of the inactive support.

2. The catalytic body of claim 1, wherein the inactive support has a porosity of 70 vol % or less.

3. The catalytic body of claim 2, wherein the inactive support is of one shape selected from the group consisting of a spherical shape, a cylindrical shape, a ring shape, a platy shape, and a combination of two or more thereof.

4. The catalytic body of claim 3, wherein the inactive support is one selected from the group consisting of alumina, silica, zirconia, silicon carbide, cordierite, and a combination of two or more thereof.

5. The catalytic body of claim 1, wherein the intermediate layer consists of one selected from the group consisting of alumina, silica, kaolin, $TiO_2$, ZnO, bentonite, and a combination of two or more thereof.

6. The catalytic body of claim 1, wherein the intermediate layer has a weight of 3 to 15 g/L with respect to a volume of the inactive support.

7. The catalytic body of claim 1, wherein the catalyst powder is an oxide derived from one selected from the group consisting of iron, magnesium, manganese, zinc, bismuth, molybdenum, and a combination of two or more thereof.

8. The catalytic body of claim 1, wherein the inorganic binder is one selected from the group consisting of alumina, silica, sodium silicate, aluminum silicate, calcium silicate, calcium carbonate, barium carbonate ($BaCO_3$), kaolin, mica, $TiO_2$, ZnO, iron oxide, bentonite, and a mixture of two or more thereof.

9. A method of manufacturing a catalytic body, comprising:
(a) mixing an inactive support and an alumina sol, followed by drying and thermal treatment to form an intermediate layer on a surface of the inactive support;
(b) dissolving two or more metal salts in a first solvent to prepare a first solution, and preparing catalyst powder by pyrolyzing the first solution while spraying the first solution into a reactor using a carrier gas or by adding a co-precipitant to the first solution and then performing drying and thermal treatment;
(c) mixing the catalyst powder, a binder, and a second solvent to prepare a second solution; and
(d) mixing the inactive support having intermediate layer formed thereon of step (a) and the second solution, followed by drying and thermal treatment to form an active layer including the catalyst powder on a surface of the intermediate layer, wherein:
the binder includes an inorganic binder;
the inorganic binder is included in an amount of 5 to 20 wt % with respect to a total weight of the catalyst powder and the inorganic binder; and
the catalyst powder has a weight of 200 to 500 g/L with respect to a volume of the inactive support.

10. The method of claim 9, wherein the inactive support has a porosity of 70 vol % or less.

11. The method of claim 10, wherein the inactive support is of one shape selected from the group consisting of a spherical shape, a cylindrical shape, a ring shape, a platy shape, and a combination of two or more thereof.

12. The method of claim 11, wherein the inactive support is one selected from the group consisting of alumina, silica, zirconia, silicon carbide, cordierite, and a combination of two or more thereof.

13. The method of claim 9, wherein the intermediate layer consists of one selected from the group consisting of alumina, silica, kaolin, $TiO_2$, ZnO, bentonite, and a combination of two or more thereof.

14. The method of claim 9, wherein the intermediate layer has a weight of 3 to 15 g/L with respect to a volume of the inactive support.

15. The method of claim 9, wherein the metal salt is a nitrate derived from one selected from the group consisting of iron, magnesium, manganese, zinc, bismuth, molybdenum, and a combination of two or more thereof.

16. The method of claim 9, wherein the co-precipitant is sodium hydroxide, ammonia, or a combination thereof.

17. The method of claim 9, wherein the pyrolysis is carried out at 500 to 900° C.

18. The method of claim 9, wherein the inorganic binder is one selected from the group consisting of alumina, silica, sodium silicate, aluminum silicate, calcium silicate, calcium carbonate, barium carbonate ($BaCO_3$), kaolin, mica, $TiO_2$, ZnO, iron oxide, bentonite, and a mixture of two or more thereof.

19. A method of preparing 1,3-butadiene comprising oxidative dehydrogenation of n-butene in the presence of the catalytic body of claim 1.

* * * * *